United States Patent
Hicks et al.

(10) Patent No.: US 10,197,824 B2
(45) Date of Patent: Feb. 5, 2019

(54) METHOD OF OBTAINING OR MAINTAINING OPTICAL TRANSMITTANCE INTO DEAERATED LIQUID

(71) Applicant: Ecolab USA Inc., St. Paul, MN (US)

(72) Inventors: Peter D. Hicks, Aurora, IL (US); Hui Li, Bolingbrook, IL (US); Michael E. Bradley, Shorewook, IL (US); Michael J. Murcia, Dekalb, IL (US); Joe L. Schwartz, Aurora, IL (US)

(73) Assignee: ECOLAB USA INC., St. Paul, MN (US)

( * ) Notice: Subject to any disclaimer, the term of this patent is extended or adjusted under 35 U.S.C. 154(b) by 781 days.

(21) Appl. No.: 14/592,219

(22) Filed: Jan. 8, 2015

(65) Prior Publication Data
US 2016/0202508 A1    Jul. 14, 2016

(51) Int. Cl.
| | |
|---|---|
| *G02F 1/11* | (2006.01) |
| *G01N 21/01* | (2006.01) |
| *G01N 21/15* | (2006.01) |
| *B08B 3/12* | (2006.01) |
| *B08B 9/027* | (2006.01) |
| *B08B 17/02* | (2006.01) |

(52) U.S. Cl.
CPC ............... *G02F 1/113* (2013.01); *B08B 3/12* (2013.01); *B08B 9/027* (2013.01); *B08B 17/02* (2013.01); *G01N 21/01* (2013.01); *G01N 21/15* (2013.01); *G01N 2021/154* (2013.01)

(58) Field of Classification Search
CPC ........ G02F 1/113; G01N 21/01; G01N 21/15; G01N 2021/154
See application file for complete search history.

(56) References Cited

U.S. PATENT DOCUMENTS

| | | | |
|---|---|---|---|
| 4,307,741 A | 12/1981 | Rossi | |
| 4,385,936 A | 5/1983 | Rossi | |
| 4,890,481 A * | 1/1990 | Ezawa | G01N 15/06 73/61.71 |
| 5,008,906 A * | 4/1991 | Reichwein | G01N 23/12 250/435 |
| 5,185,533 A | 2/1993 | Banks et al. | |
| 5,416,581 A | 5/1995 | Kanngiesser | |

(Continued)

FOREIGN PATENT DOCUMENTS

WO    WO 2014-060023 A1    4/2014

OTHER PUBLICATIONS

KIPO, International Search Report in International Patent Application No. PCT/US2012/065411, dated Mar. 18, 2013, 3 pp.

(Continued)

*Primary Examiner* — Georgia Y Epps
*Assistant Examiner* — Don Williams
(74) *Attorney, Agent, or Firm* — Leydig, Voit & Mayer, Ltd.

(57) ABSTRACT

A method of obtaining or maintaining optical transference into deaerated liquid in contact with a light transference medium is disclosed. The method comprises applying ultrasonic energy at a wavelength (λ) into deaerated liquid in contact with a light transference medium. The ultrasonic energy at wavelength (λ) originates at a distance (d) from an optical signal transmitted into the light transference medium. The distance (d) may be defined by a formula based on the wavelength (λ) of the ultrasonic energy.

19 Claims, 9 Drawing Sheets

(56) References Cited

U.S. PATENT DOCUMENTS

| | | | |
|---|---|---|---|
| 5,529,635 A | 6/1996 | Odell | |
| 5,889,209 A | 3/1999 | Piedrahita et al. | |
| 5,918,570 A * | 7/1999 | Gilchrist | B01D 19/0047 |
| | | | 122/451 R |
| 6,117,084 A | 9/2000 | Green et al. | |
| 6,217,937 B1 * | 4/2001 | Shealy | C23C 16/44 |
| | | | 118/712 |
| 6,315,909 B1 | 11/2001 | Hoots et al. | |
| 6,324,900 B1 | 12/2001 | Bruno et al. | |
| 6,336,058 B1 | 1/2002 | Fowee | |
| 6,369,894 B1 | 4/2002 | Rasimas et al. | |
| 6,452,672 B1 | 9/2002 | Trainoff | |
| 6,458,213 B1 | 10/2002 | Krieg et al. | |
| 6,572,709 B1 | 6/2003 | Kaneda et al. | |
| 6,678,045 B2 | 1/2004 | Rettig et al. | |
| 6,977,015 B2 | 12/2005 | Hardwicke et al. | |
| 7,095,500 B2 | 8/2006 | Banks | |
| 7,250,302 B2 | 7/2007 | Bernhardsson et al. | |
| 7,300,630 B2 | 11/2007 | Cronin et al. | |
| 7,341,695 B1 | 3/2008 | Garner | |
| 7,763,177 B2 | 7/2010 | Rozenberg et al. | |
| 7,799,146 B2 | 9/2010 | McLoughlin et al. | |
| 7,803,323 B2 | 9/2010 | Cronin et al. | |
| 7,808,642 B2 | 10/2010 | Connelly et al. | |
| 8,429,952 B1 | 4/2013 | Bringhurst et al. | |
| 2005/0210983 A1 | 9/2005 | Klein et al. | |
| 2006/0060787 A1 | 3/2006 | Herrington et al. | |
| 2006/0084891 A1 | 4/2006 | Barthe et al. | |
| 2007/0269366 A1 | 11/2007 | Cronin et al. | |
| 2009/0009770 A1 | 1/2009 | Connelly et al. | |
| 2009/0032733 A1 | 2/2009 | Thabeth et al. | |
| 2011/0056276 A1 | 3/2011 | Scott et al. | |
| 2013/0186188 A1 | 7/2013 | Bradley et al. | |
| 2013/0240440 A1 | 9/2013 | Maung et al. | |
| 2013/0293881 A1 | 11/2013 | Tokhtuev et al. | |

OTHER PUBLICATIONS

KIPO, Written Opinion in International Patent Application No. PCT/US2012/065411, dated Mar. 18, 2013, 5 pp.

Israel Patent Office, International Search Report in International Patent Application No. PCT/US2016/012611, dated May 11, 2016, 3 pp.

Israel Patent Office, Written Opinion in International Patent Application No. PCT/US2016/012611, dated May 11, 2016, 3 pp.

Analytical Technology, Inc., "pH/ORPMonitor: Model Q46P/R," Aug. 2013, 6 pp., Collegeville, PA.

Turner Designs, "Little Dipper In-Line Fluorometer," May 24, 2013, 17 pp., Sunnyvale, CA.

Ultrasonic Cleaning Australia, "How to degas your ultrasonic cleaner," Jun. 14, 2013, 3 pp., downloaded from http://ultrasoniccleaningaustralia.com/2013/06/14/how-to-degas-your-ultrasonic-cleaner/ on Oct. 9, 2014.

European Patent Office, Extended European Search Report in European Patent Application No. 16735460.4, 10 pp. (dated May 25, 2018).

* cited by examiner

METHOD OF OBTAINING OR MAINTAINING OPTICAL TRANSMITTANCE INTO DEAERATED LIQUID

BACKGROUND

Measurement of parameters in liquids using optical sensors is commonplace. Reliable measurement of such parameters generally requires light to pass into the liquid, which generally requires light to first pass through a reasonably transparent medium, e.g., a light transference medium. Reliability issues can arise in the event of obstruction of optical transference through the medium, which may be caused by particulate matter.

Generally, boiler liquids are deaerated liquids that have unique features. Some unique features of boiler liquids include having very low levels of dissolved oxygen (e.g., less than about 10 ppb dissolved oxygen in conventional boiler feedwater) and having a pH of from about 9 to about 11. Particularly in boiler systems utilizing a form of treatment control based on light detection and/or measurement (e.g., fluorometry), some amount of corrosion will occur over time and deposit in the form of particulate matter onto a light transference medium, thereby causing some amount of optical obstruction of the light transference medium. Regarding detection and measurement methods that utilize light transference, the unique conditions of deaerated liquids, particularly boiler liquid, present a challenge to the user when a light transference medium becomes optically obstructed. Ideally, optical obstruction can be altogether prevented, and if optical obstruction occurs, it can be removed without disrupting detection, measurement, and/or treatment control via the light transference.

SUMMARY

A method of obtaining, or of maintaining, optical transference into deaerated liquid in contact with a light transference medium is provided. The method comprises applying ultrasonic energy at a wavelength ($\lambda$) into deaerated liquid in contact with a light transference medium. The ultrasonic energy at wavelength ($\lambda$) originates at a distance (d) from an optical signal transmitted into the light transference medium such that optical transference into the deaerated liquid via the light transference medium is obtained or maintained.

BRIEF DESCRIPTION OF THE SEVERAL VIEWS OF THE DRAWING(S)

DETAILED DESCRIPTION

Figure 1:
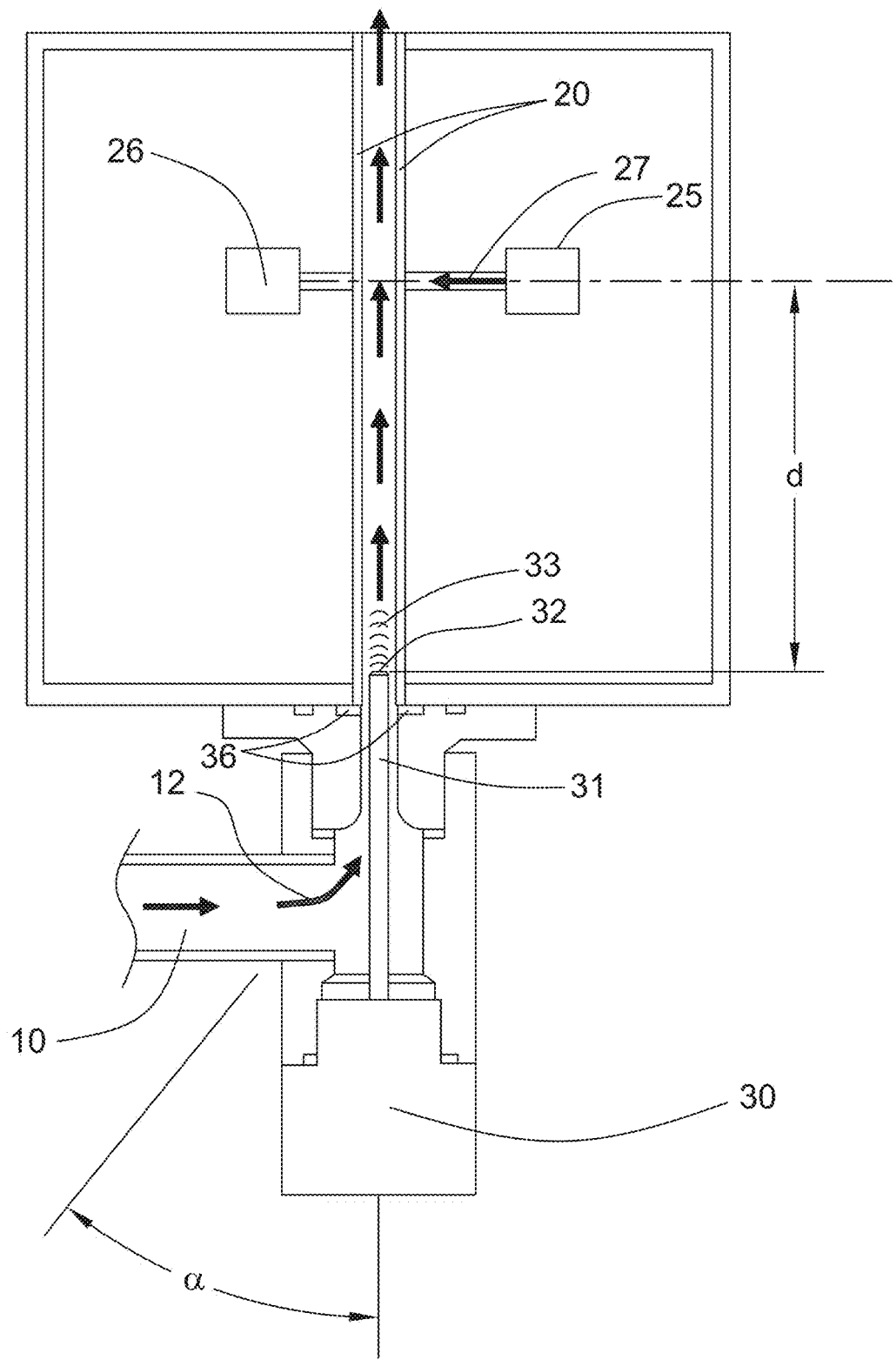
FIG. 1 illustrates an embodiment of a system capable of performing at least one inventive method described herein.

While embodiments encompassing the general inventive concepts may take various forms, there is shown in the drawings and will hereinafter be described various illustrative and preferred embodiments with the understanding that the present disclosure is to be considered an exemplification and is not intended to be limited to the specific embodiments.

A method of maintaining optical transference into deaerated (e.g., degassed) liquid in contact with a light transference medium. The method includes applying ultrasonic energy into the deaerated liquid so as to contact the light transference medium at a particular locus of points suitable for obtaining, or for maintaining, reliability in a system comprising an optical sensor. In certain embodiments, liquid is deaerated prior to being utilized in a heating application (e.g., a boiler). Liquid is generally deaerated in an attempt to minimize corrosion of metals that come in contact with the steam and/or liquid. Illustrative deaerated liquids include, but are not limited to, deaerated boiler make-up feedwater and boiler liquid, which further includes boiler blowdown liquid and boiler condensate liquid. The phrase "deaerated boiler make-up feedwater" is used to describe the boiler make-up feedwater that has undergone a deaeration process. The term is not used to describe the various boiler liquids, as it is understood by those skilled in the art that boiler liquids have already undergone a deaeration process prior to becoming boiler liquid.

As it pertains to this disclosure, unless otherwise indicated, "controller" refers to an electronic device having components such as a processor, memory device, digital storage medium, cathode ray tube, liquid crystal display, plasma display, touch screen, or other monitor, and/or other components. Controllers include, for example, an interactive interface that guides a user, provides prompts to the user, or provides information to the user regarding any portion of the method of the invention. Such information may include, for example, building of calibration models, data collection of one or more parameters, measurement location(s), management of resulting data sets, etc.

The controller is preferably operable for integration and/or communication with one or more application-specific integrated circuits, programs, computer-executable instructions or algorithms, one or more hard-wired devices, wireless devices, and/or one or more mechanical devices such as liquid handlers, hydraulic arms, servos, or other devices. Moreover, the controller is operable to integrate feedback, feed-forward, or predictive loop(s) resulting from, inter alia, the parameters measured by practicing the method(s) of the present disclosure. Some or all of the controller system functions may be at a central location, such as a network server, for communication over a local area network, wide area network, wireless network, extranet, the Internet, microwave link, infrared link, and the like, and any combinations of such links or other suitable links. In addition, other components such as a signal conditioner or system monitor may be included to facilitate signal transmission and signal-processing algorithms.

By way of example, the controller is operable to implement the method of the invention in a semi-automated or fully-automated fashion. In another embodiment, the controller is operable to implement the method in a manual or semi-manual fashion.

Data transmission of any of the measured parameters or signals to a user, chemical pumps, alarms, or other system components is accomplished using any suitable device, such as a wired or wireless network, cable, digital subscriber line, internet, etc. Any suitable interface standard(s), such as an ethernet interface, wireless interface (e.g., IEEE 802.11a/b/g/n, 802.16, Bluetooth, optical, infrared, other radiofrequency, any other suitable wireless data transmission method, and any combinations of the foregoing), universal serial bus, telephone network, the like, and combinations of such interfaces/connections may be used. As used herein, the term "network" encompasses all of these data transmission methods. Any of the components, devices, sensors, etc., herein described may be connected to one another and/or the controller using the above-described or other suitable interface or connection. In an embodiment, information (collectively referring to all of the inputs or outputs generated by the method of the invention) is received from the system and archived. In another embodiment, such information is processed according to a timetable or schedule. In a further embodiment, such information is processed in real-time. Such real-time reception may also include, for example, "streaming data" over a computer network.

As it pertains to this disclosure, unless otherwise indicated, "control scheme" refers to providing output based on input from a controller as defined herein.

A method of obtaining, or of maintaining, optical transference into deaerated liquid in contact with a light transference medium. The method comprises applying ultrasonic energy at a wavelength ($\lambda$) into deaerated liquid in contact with a light transference medium. In certain embodiments, the ultrasonic energy at wavelength ($\lambda$) originates at a distance (d) from an optical signal transmitted into the light transference medium so as to obtain or maintain optical transference into the deaerated liquid via the light transference medium. Preferably, the distance (d) is defined by Formula 1 below:

$$d=(a+0.5*n)*\lambda \qquad \text{Formula 1}$$

wherein $\lambda$ is the wavelength of the ultrasonic energy, a is a constant ranging from about −0.2 to about 0.2, and n is an integer ranging from 1 to 30. In certain embodiments, a is a constant ranging from about −0.15 to about 0.15, or from about −0.1 to about 0.1.

Ultrasonic energy follows the laws of acoustics. If the speed (v) of the ultrasonic energy is known, or approximately known, wavelength ($\lambda$) can be defined by frequency (f) according to Formula 2 below:

$$v=f*\lambda \qquad \text{Formula 2}$$

The speed (v) of the ultrasonic energy will be known or approximately known based on the medium of travel of the ultrasonic energy. For example, ultrasonic energy travels through deaerated water at a speed (v) of approximately 4800 ft/s at 68° F. (approximately 1480 m/s at 20° C.). Assuming a constant medium of travel, and therefore a constant speed (v), the frequency (f) and wavelength ($\lambda$) of the ultrasonic energy are proportionally related to one another.

The terms "optical" and "light" are used interchangeably herein. Utilization of the phrase "into deaerated liquid" is intended to cover light transmission in any direction between the deaerated liquid, the light transference medium, a light source, and/or a light detector. For example, the optical signal may originate from within the deaerated liquid and be transferred to a sensor via the light transference medium (e.g., fluorometric emission), or from a light source through the light transference medium and into the deaerated liquid (e.g., fluorometric excitation). Illustrative embodiments of optical sensors that perform optical measurements using optical signals include, but are not limited to, devices capable of detecting or sensing absorbance, colorimetric, refractometric, spectrophotometric, luminometric, and/or fluorometric signals, or images. In a preferred embodiment, the optical signal comprises a fluorometric excitation and/or emission.

The method is directed to obtaining or maintaining optical transference into deaerated liquid in contact with a light transference medium. The method can be utilized to remove obstructions that may be present on the light transference medium. Removal of obstruction from the light transference medium sufficient to allow for optical transference, thereby allowing for performance of an optical measurement of the deaerated liquid, is also achieved by the method of the present invention.

An advantage of the present invention is that the preferred method can be performed without interrupting the process responsible for supplying the deaerated liquid. For example, a boiler and its related treatment processes can continue to operate during performance of the preferred method described herein.

Ultrasonic energy is applied into deaerated liquid in contact with a light transference medium. The ultrasonic energy is applied to effectuate removal of optical obstruction that may be present on the light transference medium, particularly at a location of the light transference medium where an optical signal passes through, or should pass through.

In preferred embodiments, the deaerated liquid in contact with the light transference medium is flowing across the light transference medium as defined herein. In other embodiments, the deaerated liquid in contact with the light transference medium is not flowing across the light transference medium, i.e., is static.

In embodiments where the deaerated liquid flows across the light transference medium, the liquid may do so under conditions described as laminar, turbulent, and/or transitional flow, though the deaerated liquid may be static while in contact with the light transference medium. The deaerated liquid may have a Reynolds number of from about 0 to about 4000, including from about 400 to about 3000, and including about 800 to about 2300.

For embodiments where the deaerated liquid is flowing across the light transference medium, the ultrasonic energy may originate upstream or downstream from a location of a light transference medium where an optical signal passes through, or should pass through. In a preferred embodiment, the ultrasonic energy originates upstream from a location of a light transference medium where an optical signal passes through, or should pass through.

The ultrasonic energy may have a frequency of from about 20 kHz to about 200 kHz. The ultrasonic energy may have a frequency of from about 20 kHz, or from about 25 kHz, or from about 30 kHz, or from about 40 kHz, to about 200 kHz, or to about 150 kHz, or to about 100 kHz, or to about 80 kHz, or to about 70 kHz, or to about 60 kHz. In some embodiments, the ultrasonic energy has a frequency of from about 20 kHz to about 80 kHz. In further embodiments, the ultrasonic energy has a frequency of from about 30 kHz to about 60 kHz, which includes about 40 kHz. In even further embodiments, the ultrasonic energy has a frequency of from about 25 kHz to about 30 kHz, which includes about 28 kHz.

In certain embodiments, the ultrasonic energy is applied at a rate of from about 1 W/cm²/sec to about 400 W/cm²/sec. The ultrasonic energy may be applied at a rate of from about 1 W/cm²/sec, or from about 10 W/cm²/sec, or from about 50 W/cm²/sec, or from about 100 W/cm²/sec, to about 400 W/cm²/sec, or to about 300 W/cm²/sec, or to about 200 W/cm²/sec.

The wavelength of the ultrasonic energy is dependent upon the frequency and the velocity of the ultrasonic energy, which is essentially constant. The frequency, and therefore the wavelength, is chosen so as to provide enough energy to prevent or remove particulate matter that may become deposited onto a light transference medium in contact with deaerated liquid. Ideally, the frequency of the ultrasonic energy will be sufficient to remove such particulate matter, or prevent the particulate matter from depositing onto the light transference medium, while not damaging the light transference medium. However, a user may attempt to minimize or prevent damage to the light transference medium by utilizing one or more of several modifications discussed herein.

As described herein, the ultrasonic energy originates at a distance (d) from an optical signal transmitted into the light transference medium, which is preferably set to optimize the energy applied into the deaerated liquid at a point relative to the light transference medium, to effectively obtain or maintain light transference. Preferably, the distance (d) is defined by Formula 1 herein. For example, in embodiments that apply ultrasonic energy using an ultrasonic probe, the tip of the ultrasonic probe is located at a distance (d) such that particulate matter deposited onto the light transference medium becomes dislodged, thereby maintaining optical transference into the deaerated liquid in contact with the light transference medium. In certain embodiments, the distance (d) within certain ranges defined herein, thereby causing the ultrasonic energy to "originate" from the distance (d).

In certain embodiments, the ultrasonic energy originates at a distance of from about 30% to about 70%, or from about 35% to about 65%, or from about 40% to about 60%, of the wavelength of the ultrasonic energy. In other embodiments, the ultrasonic energy originates at a distance from an optical signal transmitted into the light transference medium of from about 80% to about 120%, or from about 85% to about 115%, or from about 90% to about 110%, of the wavelength of the ultrasonic energy. In certain embodiments, the ultrasonic energy originates at a distance of from about 130% to about 170%, or from about 135% to about 165%, or from about 140% to about 160%, of the wavelength of the ultrasonic energy. In other embodiments, the ultrasonic energy originates at a distance from an optical signal transmitted into the light transference medium of from about 180% to about 220%, or from about 185% to about 215%, or from about 190% to about 210%, of the wavelength of the ultrasonic energy. In certain embodiments, the ultrasonic energy originates at a distance of from about 230% to about 270%, or from about 235% to about 265%, or from about 240% to about 260%, of the wavelength of the ultrasonic energy. In other embodiments, the ultrasonic energy originates at a distance from an optical signal transmitted into the light transference medium of from about 280% to about 320%, or from about 285% to about 315%, or from about 290% to about 310%, of the wavelength of the ultrasonic energy. In certain embodiments, the ultrasonic energy originates at a distance of from about 330% to about 370%, or from about 335% to about 365%, or from about 340% to about 360%, of the wavelength of the ultrasonic energy. In other embodiments, the ultrasonic energy originates at a distance from an optical signal transmitted into the light transference medium of from about 380% to about 420%, or from about 385% to about 415%, or from about 390% to about 410%, of the wavelength of the ultrasonic energy. In certain embodiments, the ultrasonic energy originates at a distance of from about 430% to about 470%, or from about 435% to about 465%, or from about 440% to about 460%, of the wavelength of the ultrasonic energy. In other embodiments, the ultrasonic energy originates at a distance from an optical signal transmitted into the light transference medium of from about 480% to about 520%, or from about 485% to about 515%, or from about 490% to about 510%, of the wavelength of the ultrasonic energy.

In certain embodiments, a parameter of the deaerated liquid in contact with the light transference medium is measured by transmitting the optical signal into the deaerated liquid via the light transference medium, and detecting a response. In certain embodiments, the parameter is selected from the group consisting of: fluorescence, light absorbance, temperature, chemiluminescence, optical scattering (e.g., Rayleigh, Mie, and Raman scatter), imaging, transmittance, particle size, particle count, turbidity, and combinations thereof.

In certain embodiments, the method is a clean-in-place method. A clean-in-place method does not require disassembly of the system in order to conduct the method. In other words, the light transference medium is not removed from the system, and the system is not disconnected for the purpose of accessing the light transference medium.

In certain embodiments, treatment of the deaerated liquid is controlled by utilizing the measured parameter in a control scheme. Treatment of the deaerated liquid may include, but is not limited to, at least one of physical treatment and chemical treatment. Non-limiting examples of physical treatment include adjustment of any of the following parameters of the deaerated liquid: temperature, pressure, physical phase, flow rate (e.g., circulation, blowdown, and/or make-up), flow path, and mixing. Non-limiting examples of chemical treatment include adjustment of any of the following parameters, all related to a treatment chemical: chemical species selection, chemical species concentration, chemical species dosage rate, chemical species dosage location, and deaeration completeness.

In certain embodiments, the measured parameter is inputted into a control scheme. The control scheme is generally an automated method that inputs a plurality of several measured parameters and operates several process devices, e.g., pumps, valves, etc. For example, a certain measured parameter may indicate that treatment chemical concentration has fallen outside a lower tolerance limit. For the present example, the measured parameter may trigger the control scheme to operate a feed pump, which in turn adds treatment chemical to the process.

In certain embodiments, the optical transference through the light transference medium is at least partially obstructed by particulate matter or scaling. In some embodiments, the particulate matter may comprise a metal oxide. In certain embodiments, the light transference medium is obstructed by deposition of a chemical species selected from the group consisting of iron, copper, manganese, titanium, chromium, nickel, calcium, magnesium, oxide, phosphate, carbonate, silicate, and combinations thereof. In certain embodiments, the light transference medium is obstructed by scale comprising a chemical species selected from the group consisting of calcium, magnesium, phosphate, carbonate, silicate, and combinations thereof.

In other embodiments, the particulate deposition may comprise particulate matter found in raw water, e.g., mud, sand, silt, etc.

In certain embodiments, the deaerated liquid may be conditioned prior to contacting the light transference medium. For example, particularly when the deaerated liquid is boiler blowdown liquid or boiler condensate liquid, the deaerated liquid may be "enthalpy-rich." At elevated temperature and pressure (e.g., 300-1500° F. and corresponding pressures for saturated steam/liquid), the deaerated liquid may be conditioned such that a portion of the enthalpy (measured in the form of temperature and pressure) are removed prior to the deaerated liquid contacting the light transference medium. In certain embodiments, the deaerated liquid in contact with the light transference medium has a temperature of from about 20° F. to about 200° F., including from about 40° F. to about 150° F., and including from about 60° F. to about 130° F. In certain embodiments, the deaerated liquid in contact with the light transference medium has a pressure of from about 5 psig to about 100 psig, including from about 10 psig to about 70 psig, and including from about 15 psig to about 50 psig.

The timing of the application of the ultrasonic energy to the deaerated liquid may take any one or more of several forms. In one embodiment, the ultrasonic energy is continuously streamed into the deaerated liquid, which preferably includes while the system utilizing the deaerated liquid is operational. In another embodiment, the ultrasonic energy is applied intermittently, e.g., for a timed duration at timed intervals. In yet another embodiment, the ultrasonic energy is applied on an as-needed basis, which can be determined, e.g., by comparing historical data related to the relevant sensor and light transference medium. For example, if obstruction of the light transference medium grows to an unacceptable value, e.g., a setpoint of from about 1 to about 5% obstruction, ultrasonic energy is then applied to the wetted surface of the light transference medium as described herein.

Examples of light transference media include a flow cell, an optical window, a reflective surface, a refractive surface, a dispersive element, a filtering element, and an optical fiber sensor head. In embodiments where the light transference medium is transparent or nearly transparent, the light transference medium is generally constructed of a material that is transparent or nearly transparent and having a hardness of at least about 7 on the Mohs scale. The term "transparent or nearly transparent" refers to the ability of light to pass through a substance sufficient to use light for detection and/or measurement purposes as discussed herein, which includes transparency as defined by ASTM D1746. In certain embodiments, the light transference medium is constructed of quartz, sapphire, diamond, or boron nitride.

In certain embodiments, the light transference medium is constructed of any suitable transparent or nearly transparent composition, and is coated with a transparent or nearly transparent substance having a hardness of at least about 7 on the Mohs scale. For example, the light transference medium may be constructed of a substance having a Mohs scale hardness of at least about 7 (e.g., quartz), and then coated with a substance having an even higher Mohs scale rating. In certain embodiments, the coating substance has a Mohs scale rating of from about 8 to 10, or from about 9 to 10, or 10. Illustrative embodiments of substances suitable for coating a light transference medium include, but are not limited to, diamond, titanium diboride, boron nitride, and sapphire.

In certain embodiments, the light transference medium takes the form of a reflective surface. In embodiments utilizing a reflective surface, an optical window may be utilized in concert with the reflective surface to provide observation from outside the deaerated liquid.

FIG. 1 illustrates a system capable of performing the inventive method. A deaerated liquid 10, which flows in a direction 12, contacts a light transference medium 20. Light transference medium 20 is a flow cell, and deaerated liquid 10 flows through the flow cell via direction 12. A light source 25 and a detector 26 are located so as to transmit an optical signal 27 through light transference medium 20 and deaerated liquid 10, and detect the resulting behavior caused by the transmitted optical signal 27, which may include fluorescence, light absorbance, temperature, chemiluminescence, optical scattering (e.g., Rayleigh, Mie, and Raman scatter), imaging, transmittance, particle size, particle count, turbidity, and combinations thereof. An ultrasonic transducer 30 is operably attached to an ultrasonic probe 31 having a tip 32 that emits ultrasonic energy 33 at a wavelength ($\lambda$), with tip 32 being located at a distance (d) from the optical signal 27, with distance (d) being defined by Formula 1 presented herein. Optionally, the ultrasonic probe 31 may be positioned such that tip 32 emits ultrasonic energy 33 at an angle $\alpha$ of from 0 to about 45 degrees, or to about 35 degrees, or to about 25 degrees, or to about 15 degrees, or to about 5 degrees, as illustrated. In certain embodiments, the ultrasonic probe 31 is positioned such that tip 32 projects ultrasonic energy 33 substantially in the direction of flow 12 of deaerated liquid 10 across light transference medium 20. FIGS. 1, 2, 4, 5A, and 5B illustrate embodiments including a mount that seals ultrasonic transducer 30 to light transference medium 20 utilizing a seal 36, which in certain embodiments is a washer. In certain embodiments, seal 36 is constructed of an elastomer. Exemplary embodiments of elastomers include, but are not limited to, nitrile-butadiene rubber ("nitrile"), hydrogenated nitrile-butadiene rubber, ethylene propylene diene monomer ("EPDM"), silicone, fluoroelastomer, and polychloroprene.

Figure 2:
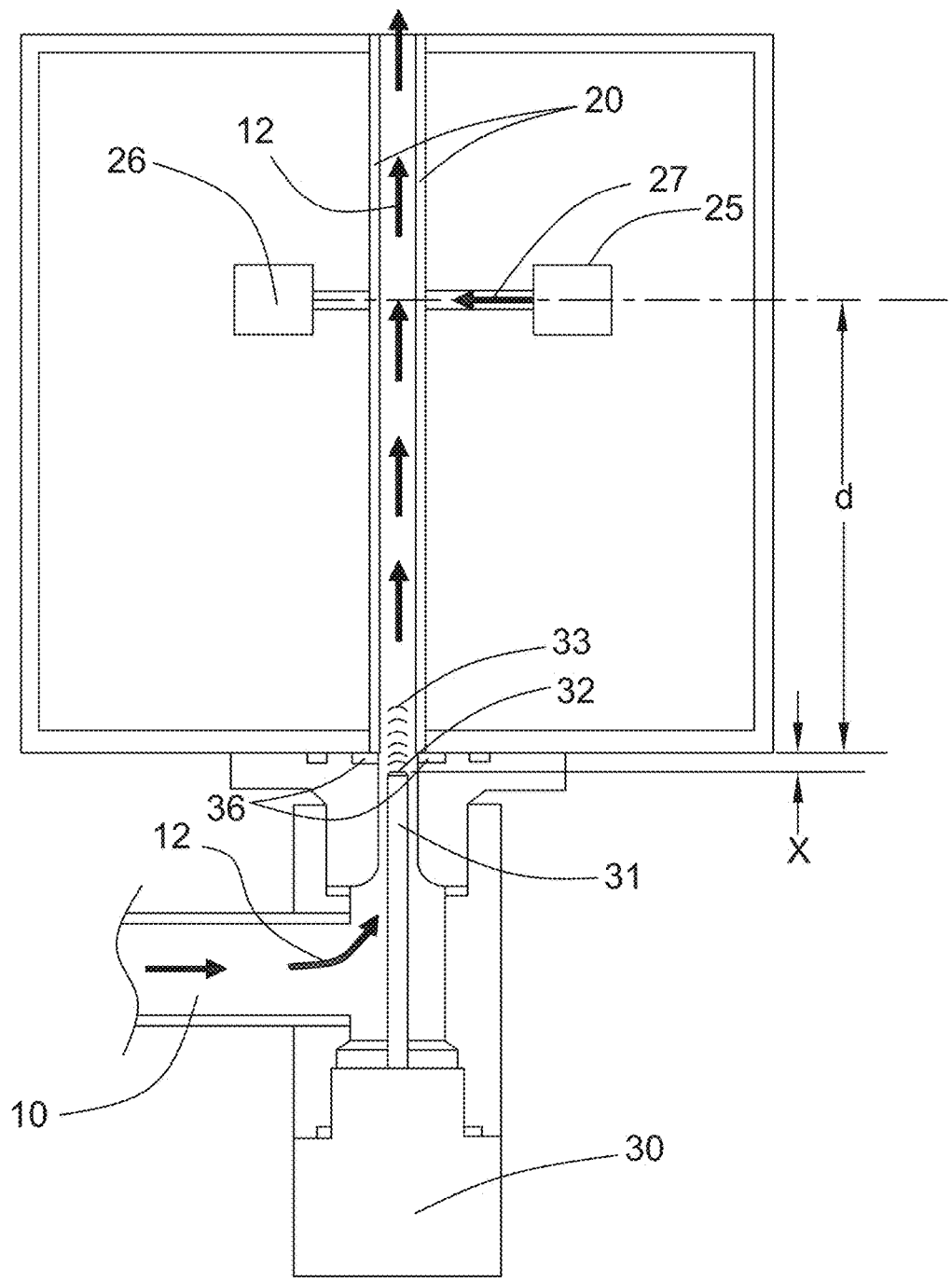
FIG. 2 illustrates a variation of the illustrative embodiment shown in FIG. 1.

FIG. 2 illustrates an embodiment, wherein the tip 32 of the ultrasonic probe 31 is positioned so as to create an offset X from light transference medium 20. Utilization of offset X can be of particular importance to allow sufficient ultrasonic energy at wavelength ($\lambda$) into the light transference medium when a relatively soft material (e.g., seal 36) is present in the direction of the ultrasonic energy. The ultrasonic energy will be less likely to be dampened by the relatively soft material due to the low energy level at the location of the relatively soft material. In embodiments that incorporate a relatively soft material between an ultrasonic probe 31 and a light transference medium 20, the distance (d) should be measured from a point beyond the relatively soft material to light transference medium 20, as illustrated in FIG. 2. In certain embodiments utilizing offset X, offset X is defined by Formula 3 below:

$$X=(b+0.25*(2n-1))*\lambda \qquad \text{Formula 3}$$

wherein $\lambda$ is the wavelength of the ultrasonic energy, b is a constant ranging from about −0.2 to about 0.2, and n is an integer ranging from 1 to 30. In certain embodiments, b is a constant ranging from about −0.15 to about 0.15, or from about −0.1 to about 0.1.

Figure 3:
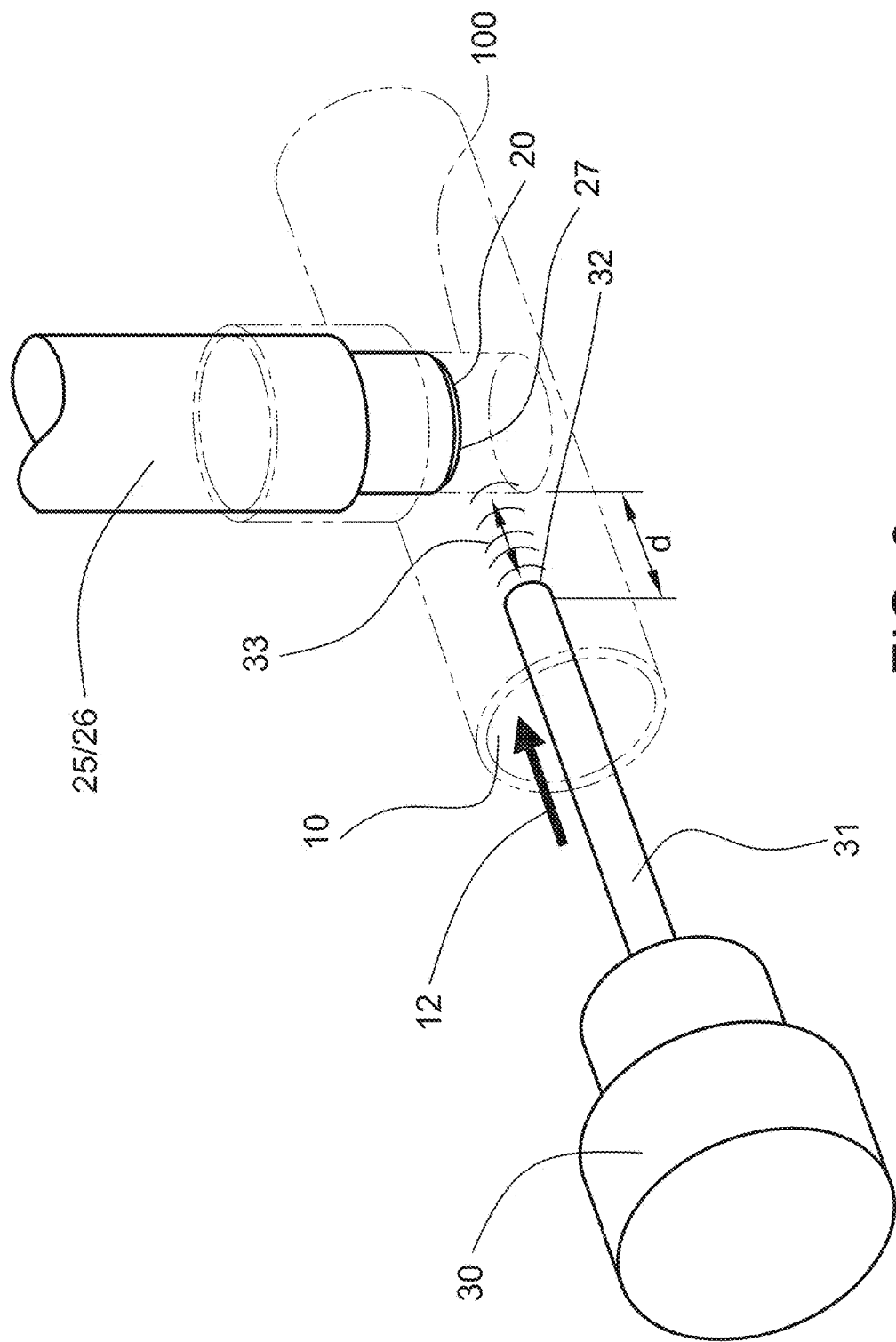
FIG. 3 illustrates an embodiment of a system capable of performing at least one inventive method described herein.

FIG. 3 illustrates yet another embodiment of a system capable of performing the inventive method. A deaerated liquid 10, which flows in a direction 12, contacts a light transference medium 20, which can be, for example, mounted via a tee pipe fitting 100. Light transference medium 20 takes the form of an optical window of a combination light source/detector 25/26, and deaerated liquid 10 flows across the optical window. Combination light source/detector 25/26 is located so as to transmit an optical signal 27 through light transference medium 20 (the optical window) and into the deaerated liquid 10, and detect the resulting behavior caused by optical signal 27, which may include fluorescence, light absorbance, temperature, chemiluminescence, optical scattering (e.g., Rayleigh, Mie, and Raman scatter), imaging, transmittance, particle size, particle count, turbidity, and combinations thereof. While FIG. 3 shows an embodiment utilizing a combination light source/detector 25/26, a person skilled in the art will readily recognize that the light source and the detector may be separate units operably connected to a control unit (not shown). An ultrasonic transducer 30 is operably attached to an ultrasonic probe 31 having a tip 32 that emits ultrasonic energy 33, with tip 32 being located at a distance (d) from the optical signal 27, with distance (d) defined by Formula 1 presented herein.

Figure 4:
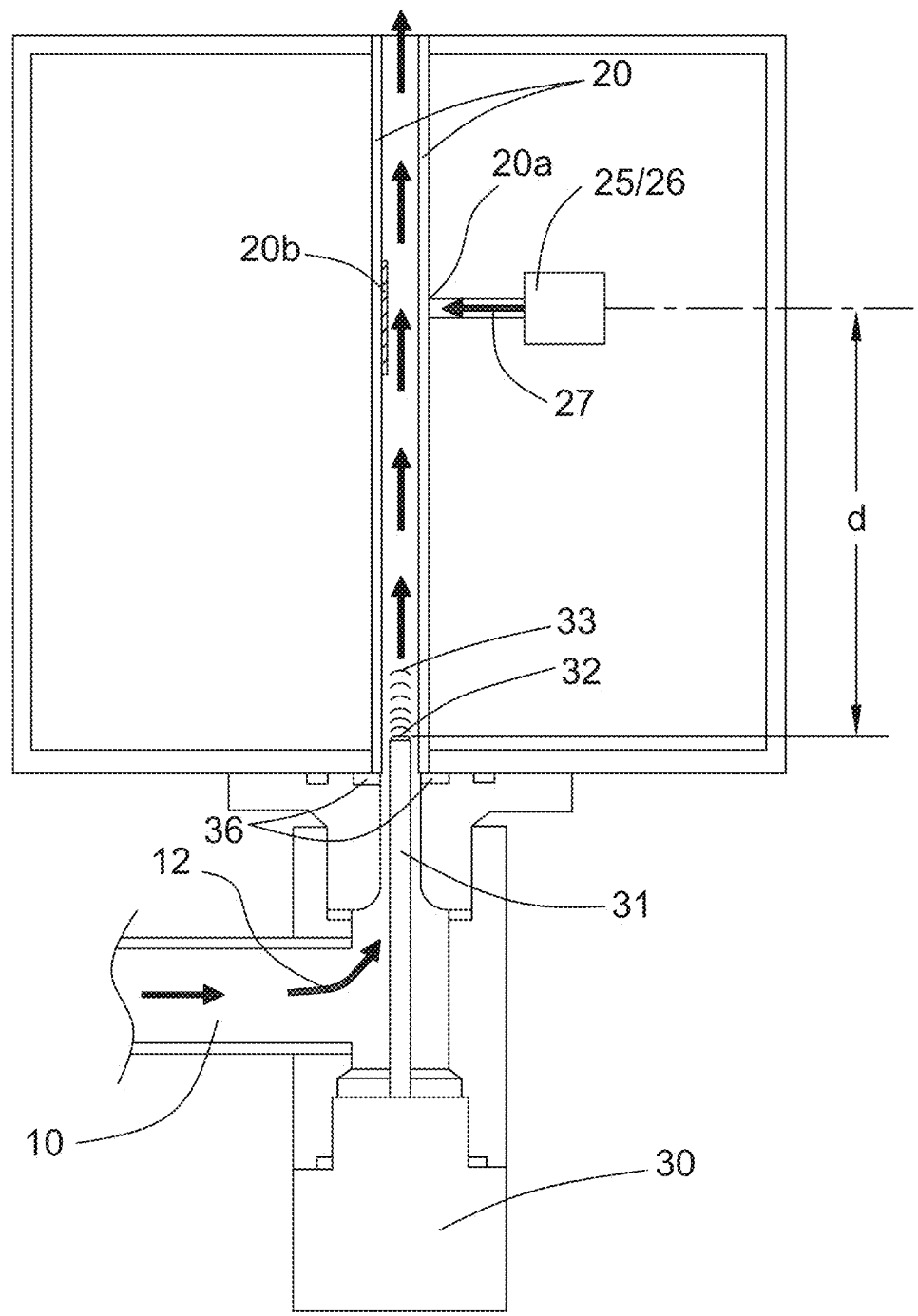
FIG. 4 illustrates an embodiment of a system capable of performing at least one inventive method described herein.

FIG. 4 illustrates a further embodiment of a system capable of performing the inventive method is illustrated. A deaerated liquid 10, which may flow in a direction 12, contacts a light transference medium 20. Light transference medium 20 includes a transparent portion 20a and an optional reflective portion 20b, and deaerated liquid 10 contacts each of transparent portion 20a and reflective portion 20b. A combination light source/detector 25/26 is located so as to transmit an optical signal 27 through transparent portion 20a and into deaerated liquid 10, and detect the resulting behavior caused by optical signal 27, which may include fluorescence, light absorbance, temperature, chemiluminescence, optical scattering (e.g., Rayleigh, Mie, and Raman scatter), imaging, transmittance, particle size, particle count, turbidity, and combinations thereof. Optical signal 27 may be transmitted from combination light source/detector 25/26 via optical fibers capable of receiving and transmitting fluorescent emission to the combination light source/detector 25/26. Alternately, the system may be configured to utilize a light source 25 and detector 26 in addition to or in place of the combination light source/detector 25/26, wherein light source 25 and detector 26 are not aligned opposite one another. While a combination light source/detector 25/26 is illustrated in this particular embodiment, a person of skill in the art will readily recognize that the light source and the detector may be separate units connected to a control unit (not shown). An ultrasonic transducer 30 is operably attached to an ultrasonic probe 31 having a tip 32 that emits ultrasonic energy 33, with tip 32 located at a distance (d) from optical signal 27, with distance (d) being defined by Formula 1 presented herein.

In certain embodiments, an enhancer is utilized to assist in performing the methods described herein. When utilized, the enhancer allows ultrasonic energy to be applied in a manner that provides beneficial removal of obstruction while protecting the light transference medium from damage that may be caused by the application of ultrasonic energy. Particularly when applied at sharp angles (e.g., perpendicular) toward the light transference medium, ultrasonic energy can damage the light transference medium. The utilization of one or more enhancers can limit or prevent the occurrence of such damage. When utilized, the enhancer may comprise at least one of a sleeve and a lossy surface. It is important to note that these particular enhancers may be used individually or in combination, or in some embodiments of the methods, not used at all. Whether to use an enhancer depends on a number of factors, including, but not limited to, the durability of the light transference medium, and the angle and frequency of the ultrasonic energy.

In embodiments utilizing a sleeve as an enhancer, the sleeve is generally positioned so as to protect a portion of the light transference medium located near the source of ultrasonic energy. Generally, the sleeve is constructed and positioned so as to prevent dampening of the ultrasonic energy in the vicinity of the transmission of the optical signal into the light transference medium. More particularly, the sleeve should protect the light transference medium from damage that may be caused by ultrasonic energy traveling perpendicular or nearly perpendicular from the ultrasonic energy source toward the light transference medium. When utilized, the sleeve should be constructed of a material suitable for providing protection to the light transference medium. For example, the sleeve may be constructed of stainless steel.

Figure 5A:
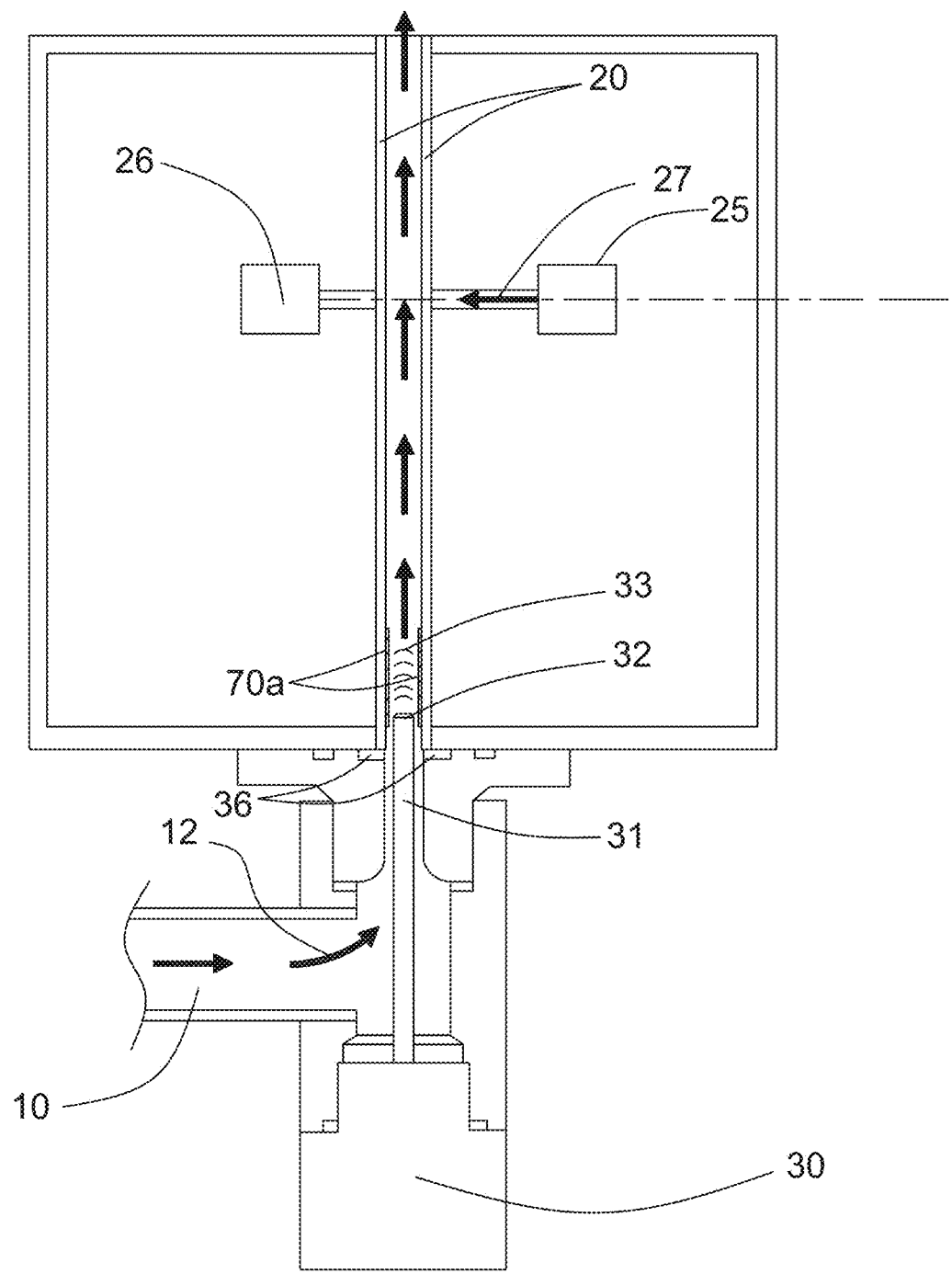
FIG. 5A illustrates an embodiment of a system incorporating a sleeve as described herein.

In other embodiments, the sleeve is constructed of a substance that is not completely rigid, but is not so soft as to absorb an undesired amount of the ultrasonic energy. For example, in embodiments that utilize a sleeve, the sleeve may be constructed of a substance compatible with contacting liquid(s). Furthermore, the sleeve may be constructed of a substance having a Shore "A" hardness of from about 60 to about 90. In certain embodiments, the sleeve is constructed of an elastomer as defined herein. FIG. 5A demonstrates an illustrative embodiment of a system that incorporates sleeve 70a into its design. Example 3 provides further information related to an embodiment of a sleeve utilized to prevent over-dampening.

Figure 5B:
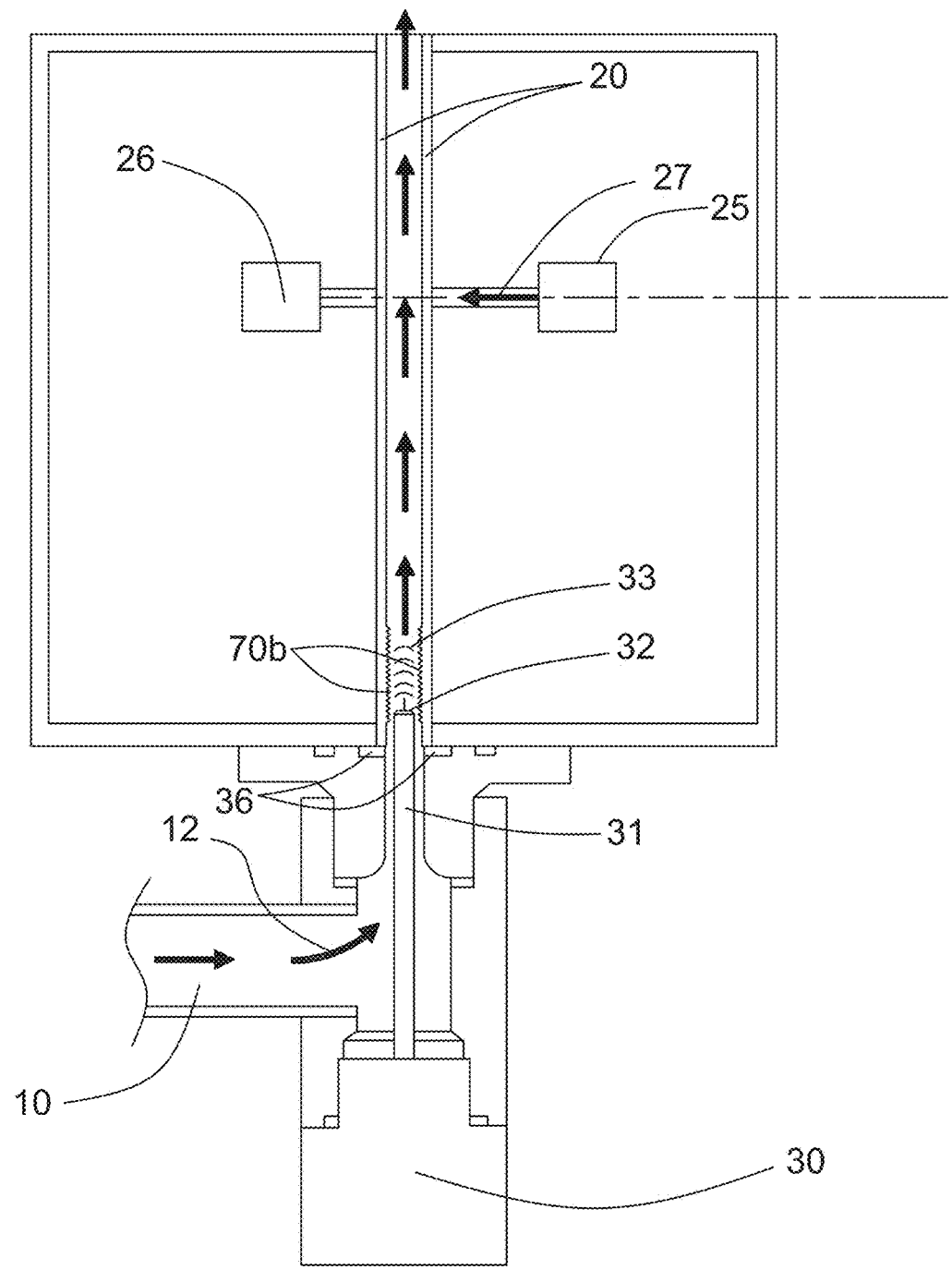
FIG. 5B illustrates an embodiment of a system incorporating a lossy surface.

In embodiments utilizing a lossy surface as an enhancer, the lossy surface is generally positioned so as to protect a portion of the light transference medium located near the source of ultrasonic energy. Generally, the lossy surface is positioned so as to dampen a portion of the ultrasonic energy traveling toward the light transference medium, and particularly the ultrasonic energy traveling perpendicular or nearly perpendicular from the ultrasonic energy source toward the light transference medium. In certain embodiments, the lossy surface is a surface that is generally rough, such as, e.g., a grooved, threaded, or jagged surface. Generally, a lossy surface is rough such that at least a portion of the ultrasonic energy is scattered away when coming in contact with the lossy surface. FIG. 5B demonstrates an illustrative embodiment of a system that incorporates lossy surface 70b into its design.

The following examples further illustrate the invention but, of course, should not be construed as in any way limiting its scope.

EXAMPLE 1

Figure 6:
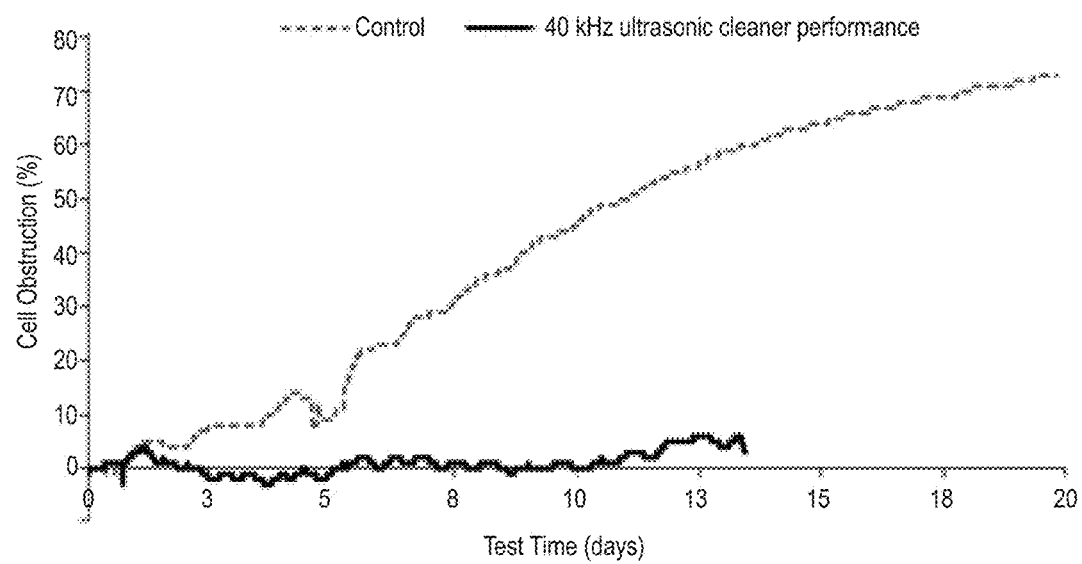
FIG. 6 is a plot of experimental data collected during the execution of Example 1.

FIG. 6 is a plot of obstruction of light transference media in the form of particulate deposition onto flow cells. Two light transference media (flow cells for this Example) were used to perform the experiment: ultrasonic energy was applied to the test flow cell, and no cleaning method was implemented for the control flow cell. In the example, the flow cells were initially clean and of the same type. The flow cells were exposed to the same blowdown stream of a 1500 psi recovery boiler of a paper mill. The flow cells were quartz glass tubes, each having an outer diameter of 0.312" (7.9 mm), an inner diameter of 0.236" (6 mm), and a length of 4.69" (11.9 cm). The ultrasonic energy was applied via a probe positioned at a distance (d) of 58 mm according to FIG. 1 and Formula 1 (i.e., n=3), with the tip of the ultrasonic probe positioned flush with the end of the light transference medium. The blowdown of the recovery boiler flowed through the flow cells after being conditioned from saturated, e.g., 1515 psig at 597° F., to less than 40 psig and less than 120° F. The conditioned blowdown is expected to flow through the flow cells under laminar flow, as the flow rate is approximately 500 mL/min and having a Reynolds Number of approximately 1800.

Ultrasonic energy was applied to the test flow cell at 40 kHz, which was intermittently applied at 2.2% duty. In other words, the ultrasonic energy was applied to the test flow cell for 1 minute per 45 minutes (i.e., 1 minute/45 minutes=0.022).

The experiment was carried out over 20 days for the control flow cell, which continued to accumulate particulate deposition up to about 75% obstruction. The experiment was carried out over 14 days for the test flow cell, which accumulated virtually no obstruction over the 14-day trial. Obstruction of the light transference medium was virtually eliminated by the application of ultrasonic energy at a frequency of 40 kHz.

EXAMPLE 2

Figure 7:
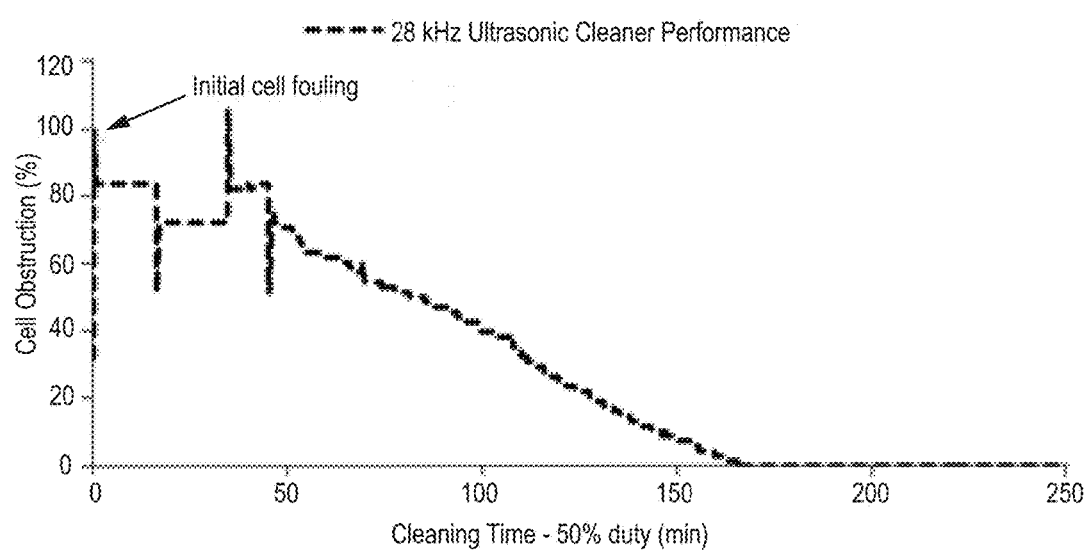
FIG. 7 is a plot of experimental data collected during the execution of Example 2.

FIG. 7 is a plot of particulate deposition being removed from a light transference medium, in this instance a flow cell, over time by the application of ultrasonic energy to the flow cell. In the example, the flow cell was exposed to a blowdown stream of a powerhouse boiler. The flow cell was the same as the test flow cell of Example 1 herein, except that the distance (d) was 56 mm, and the tip of the ultrasonic probe was 10 mm beyond the end of the flow cell (offset (X)=10 mm) as shown in FIG. 2. Offset (X) fits Formula 3, with n=1. The flow cell was approximately 100% obstructed at the beginning of the experiment. Blowdown of the powerhouse boiler flowed through the flow cell at 300 mL/min after being conditioned as in Example 1 herein.

Ultrasonic energy was applied to the flow cell at 28 kHz, which was intermittently applied at 50% duty (i.e., one minute "on" for every minute "off"), as opposed to the 2.2% duty to the test flow cell of Example 1. The experiment was carried out over approximately 250 minutes. By approximately the 170$^{th}$ minute, substantially all of the particulate deposition had been removed, and the flow cell was substantially unobstructed.

EXAMPLE 3

Figure 8:
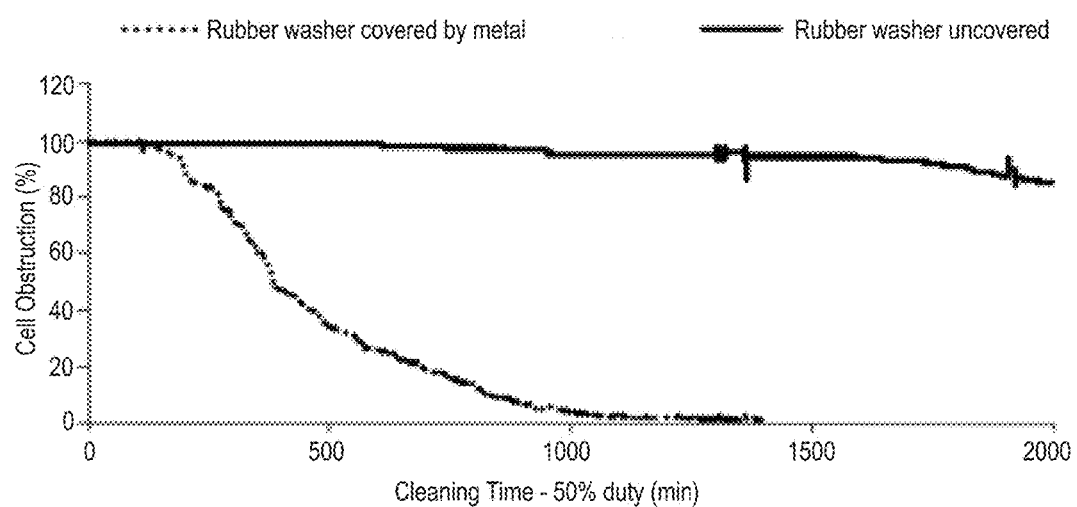
FIG. 8 is a plot of experimental data collected during the execution of Example 3.

FIG. 8 is a plot of the effect of the utilization of an enhancer in combination with an EPDM washer used to seal the ultrasonic energy source to a light transference medium, for this Example flow cells as described in Examples 1 and 2 herein. Each EPDM washer used to seal the flow cells had a Shore "A" hardness of about 55 to about 75. For this Example, the enhancer was a sleeve covering the EPDM washer and part of the light transference medium of the test flow cell. The control flow cell incorporated the EPDM washer seal but did not incorporate an enhancer. In the example, each of the two flow cells were initially 100% obstructed by particulate deposition and were exposed to the same conditioned blowdown stream as in Examples 1 and 2, except that the pre-conditioned blowdown stream was initially saturated at 700 psig and 503° F. The conditioned blowdown stream (less than 40 psig and less than 120° F.) flowed through the flow cells at approximately 300 mL/min. Ultrasonic energy was applied to both the control flow cell and the test flow cell. The distance (d) for the test flow cell was 62 mm, and the tip of the ultrasonic probe was 6 mm beyond each flow cell (offset (X)=6 mm, but only for the control flow cell). Because the EPDM washer was covered by an enhancer for the test flow cell, the distance (d) followed FIG. 1 and Formula 1, with n=2. For the control flow cell, the distance (d) was 56 mm and offset (X) was 6 mm, as shown in FIG. 2, which falls within the parameters of Formula 3. However, incorporation of the enhancer of the test flow cell was clearly beneficial in minimizing the dampening effect of the EPDM washer.

The sleeve was constructed of 316-stainless steel "thin wall" tubing, having an outer diameter slightly less than the 0.236" inner diameter of the test flow cell. The ultrasonic energy was applied to each flow cell at 20 kHz, which was intermittently applied at 50% duty. As shown in FIG. 8, the control sample showed little removal of obstruction at 20 kHz at 50% duty for the 2000-minute test. However, utilization of a sleeve covering the EPDM washer and a portion of the test flow cell allowed for nearly complete removal of the obstruction after about 1000 minutes of 20 kHz ultrasonic energy at 50% duty.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and "at least one" and similar referents in the context of describing the invention (especially in the context of the following claims) are to be construed to cover both the singular and the plural, unless otherwise indicated herein or clearly contradicted by context. The use of the term "at least one" followed by a list of one or more items (for example, "at least one of A and B") is to be construed to mean one item selected from the listed items (A or B) or any combination of two or more of the listed items (A and B), unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as," "illustrative") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

What is claimed is:

1. A method of obtaining or maintaining optical transference into deaerated liquid in contact with a light transference medium, the method comprising:
applying ultrasonic energy at a wavelength (λ) into deaerated liquid in contact with a light transference medium, the ultrasonic energy at wavelength (λ) originating at a distance (d) from an optical signal transmitted into the light transference medium to obtain or maintain optical transference into the deaerated liquid via the light transference medium,
wherein the distance (d) defined by the formula:

$$d=(a+0.5*n)*\lambda,$$

wherein λ=the wavelength of the ultrasonic energy, a is a constant ranging from about −0.2 to about 0.2, and n is an integer ranging from 1 to 30.

2. The method of claim 1, further comprising measuring a parameter of the deaerated liquid in contact with the light transference medium by transmitting the optical signal into the deaerated liquid via the light transference medium, and detecting a response.

3. The method of claim 2, further comprising controlling treatment of the deaerated liquid by utilizing the measured parameter in a control scheme.

4. The method of claim 3, wherein the method is performed during operation of a system utilizing the deaerated liquid.

5. The method of claim 1, wherein the optical transference through the light transference medium is obstructed prior to the application of the ultrasonic energy to the light transference medium.

6. The method of claim 1, wherein the deaerated liquid is at least one of deaerated boiler make-up feedwater, boiler condensate, and boiler blowdown liquid.

7. The method of claim 1, wherein the light transference medium is obstructed by deposition of a chemical species selected from the group consisting of iron, copper, manganese, titanium, chromium, nickel, calcium, magnesium, oxide, phosphate, carbonate, silicate, and combinations thereof.

8. The method of claim 1, wherein the light transference medium is obstructed by scale comprising a chemical species selected from the group consisting of calcium, magnesium, phosphate, carbonate, silicate, and combinations thereof.

9. The method of claim 1, wherein the ultrasonic energy is applied in a manner selected from the group consisting of: continuous, intermittent, as-needed, and combinations thereof.

10. The method of claim 1, wherein the ultrasonic energy is applied at a rate of from about 1 $W/cm^2$/sec to about 400 $W/cm^2$/sec.

11. The method of claim 1, wherein the ultrasonic energy is applied at a frequency of from about 20 kHz to about 200 kHz.

12. The method of claim 1, wherein the light transference medium is selected from the group consisting of: a flow cell, an optical window, and a reflective surface.

13. The method of claim 1, wherein the light transference medium has a Mohs scale hardness of at least about 7.

14. The method of claim 1, wherein the light transference medium is constructed of a material selected from the group consisting of quartz, sapphire, diamond, boron nitride, and derivatives thereof.

15. The method of claim 1, wherein the light transference medium is a quartz flow cell coated with at least one of diamond, titanium diboride, boron nitride, and derivatives thereof.

16. The method of claim 1, wherein method is a clean-in-place method.

17. The method of claim 1, wherein an enhancer protects at least a portion of the light transference medium from the ultrasonic energy source.

18. The method of claim 17, wherein the enhancer comprises at least one of a sleeve and a lossy surface.

19. The method of claim 1, wherein the deaerated liquid contacts the light transference medium at a pressure of from about 5 psig to about 100 psig, and at a temperature of from about 20° F. to about 200° F.

* * * * *